(12) United States Patent
Edelhauser et al.

(10) Patent No.: US 9,017,339 B2
(45) Date of Patent: Apr. 28, 2015

(54) MEASUREMENT DEVICE FOR EXTERNAL FIXATION FRAME

(75) Inventors: Adam John Edelhauser, Nyack, NY (US); Jan Heinsohn, Hoboken, NJ (US)

(73) Assignee: Stryker Trauma GmbH (DE)

( * ) Notice: Subject to any disclaimer, the term of this patent is extended or adjusted under 35 U.S.C. 154(b) by 389 days.

(21) Appl. No.: 13/456,666

(22) Filed: Apr. 26, 2012

(65) Prior Publication Data

US 2013/0289575 A1 Oct. 31, 2013

(51) Int. Cl.
*A61B 17/58* (2006.01)
*A61F 2/00* (2006.01)
*A61B 17/70* (2006.01)

(52) U.S. Cl.
CPC .................................. *A61B 17/7074* (2013.01)

(58) Field of Classification Search
CPC ... A61B 19/46; A61B 17/62; A61B 2019/467
USPC .......... 606/54–59, 102, 1, 129, 130;
600/587–595; 33/511, 512, 471, 532, 33/538, 1 N
See application file for complete search history.

(56) References Cited

U.S. PATENT DOCUMENTS

| | | | |
|---|---|---|---|
| 1,590,499 A * | 6/1926 | Cozad | 600/595 |
| 3,807,050 A | 4/1974 | Showalter | |
| 4,365,624 A | 12/1982 | Jaquet | |
| 4,615,338 A | 10/1986 | Ilizarov et al. | |
| 4,978,348 A | 12/1990 | Ilizarov | |
| 5,663,533 A * | 9/1997 | Judge | 181/141 |
| 5,702,389 A | 12/1997 | Taylor et al. | |
| 5,961,555 A | 10/1999 | Huebner | |
| 5,971,984 A * | 10/1999 | Taylor et al. | 606/54 |
| 6,505,412 B2 | 1/2003 | Hauzie, Jr. | |
| 2005/0149038 A1 | 7/2005 | Haines et al. | |
| 2008/0300605 A1 | 12/2008 | Rinner | |
| 2009/0038168 A1 * | 2/2009 | Wixey | 33/471 |
| 2010/0234844 A1 | 9/2010 | Edelhauser et al. | |
| 2012/0330312 A1 | 12/2012 | Burgherr et al. | |

FOREIGN PATENT DOCUMENTS

DE 10014397 A1 10/2001
WO 2012107061 A1 8/2012

OTHER PUBLICATIONS

Extended European Search Report for Application No. EP13164481 dated Aug. 3, 2013.

* cited by examiner

*Primary Examiner* — Todd Manahan
*Assistant Examiner* — Jessica Weiss
(74) *Attorney, Agent, or Firm* — Lerner, David, Littenberg, Krumholz & Mentlik, LLP (57) ABSTRACT

A protractor for use with an external fixation frame is provided. The protractor may include a face having angle designations thereon and a set of opposed and extending flanges projecting from said face. The flanges may connect to a portion of an external fixation frame, such as a ring (or other component) of the frame. The face may also include a post member to which a rotatable dial is mounted. An elongate member may be pivotally connected to a portion of the post member and may include a clamp. The clamp may be used to connect to an alternate portion of an external fixation frame, such as a strut of the frame. Thus, the protractor may be connected to two points on an external fixation frame so as to measure the angle between such points. Related methods of using the aforementioned protractor are also disclosed.

13 Claims, 6 Drawing Sheets

FIG. 7

MEASUREMENT DEVICE FOR EXTERNAL FIXATION FRAME

FIELD OF THE INVENTION

The present invention relates generally to measuring devices that may be used to measure the angle between respective portions of a medical device, and in particular to protractor-type devices for measuring the angle between respective portions of an external fixation frame.

BACKGROUND OF THE INVENTION

In the external fixation industry, it is often necessary to realign, reposition, and/or securely hold two bone elements relative to one another. For example, in the practice of medicine, bone fragments and the like must sometimes be aligned or realigned and repositioned to restore boney continuity and skeletal function. External fixators may be utilized for this purpose, e.g., such fixators may be used to treat several injuries and/or deformities, including: acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

Generally, the external fixation market can be divided into two major segments: (1) acute trauma, and (2) reconstructive. The customers, products, and needs of each segment may vary widely. Specifically, the trauma segment is dominated by modular fixators. These frames are generally characterized by very rapid application, and, consequently, are known for being fairly simple products. Typically, most of these frames are used for temporary fixation and quite often are only on the patient for hours or days.

The reconstructive segment leans heavily toward ring fixation. Ring fixators, such as the well known Ilizarov frame, are very popular. Such frames are shown in U.S. Pat. Nos. 4,365,624; 4,615,338; 4,978,348; 5,702,389; and 5,971,984, the disclosures of which are hereby incorporated by reference in their entireties. Ring fixators can accomplish a full six degrees of freedom and, when applied and managed well, can aid the correction of primary deformities while not creating secondary deformities. However, mastery of the products themselves and related techniques for use can be a long and daunting process that is not attractive to many users.

In particular, during treatment via an external fixator, potentially of the type described above, the fixator is typically adjusted over a period of time (e.g., during treatment) to reposition bone segments. This adjustment may be implemented according to a "prescription" or correction plan. For example, physicians may adjust an external fixator at precise times over a period of treatment (e.g., on a daily basis for three weeks). Patients, however, may not desire to visit the physician's office every time an adjustment is needed. For this reason, many external fixators can be adjusted by the patients themselves without the assistance of a physician. Adjustment of the external fixator in this manner should nonetheless strictly comply with a predetermined correction or "prescription" plan. On some occasions, however, patients may not adjust their external fixator according to the correction plan for a variety of reasons. For instance, patients may not understand how to use the external fixator correctly. In addition, when the patients themselves adjust the external fixators, physicians may not even know whether patients are in fact adjusting the external fixators according to the correction plan.

To ensure that a particular correction plan is adhered to, it is beneficial for a user (e.g., the surgeon or the patient, depending) to be able to determine the angle between a strut of the external fixator and a ring (or rings) to which the strut is attached. For instance, an external fixation frame, potentially of the Ilizarov-type described above, may include struts, which are aligned at a particular angle with respect to a ring (or rings) used in the frame. Thus, to ensure proper healing and/or correction of a deformity, a user of the frame (e.g., the surgeon or patient) may need to determine such angles. Periodically, these angles may also be modified so as to conform to a predetermined correction plan, as noted above.

As such, it is an object of the present invention to provide improved devices and methods for measuring the angle between two or more points on an external fixation frame and for adjusting an external fixation frame using such devices.

BRIEF SUMMARY OF THE INVENTION

One aspect of the present invention provides an instrument for determining an angle between a first portion and a second portion of an external fixation device. In some embodiments, the instrument may comprise a face having a connector for engaging the face to the first portion of the external fixation device, a rotatable dial mounted to the face, and an elongate member pivotally coupled to the rotatable dial. The instrument may further include a coupling engaged to the elongate member for connecting to the second portion of the external fixation device. The first portion of the external fixation device may also be rotatably connected to the second portion of the external fixation device.

Particular embodiments of this first aspect may also include a connector on the face having a set of opposed and extending flanges, the flanges defining a channel sized to receive the first portion of the external fixation device. Further, these embodiments may include a coupling in the form of a clamp sized to engage the second portion of the external fixation device, which, in some instances, may be a portion of a length of a strut.

Another aspect of the present invention includes an instrument for use with an external fixation device that comprises a face with a plurality of angle designations thereon, and a connector for engaging the face to the external fixation device, the connector including opposed projections spaced apart from one another, such that the projections are attachable to a first portion of the external fixation device. The instrument may also comprise a rotatable dial mounted to a post member engaged with the face, the dial being rotatable in conjunction with the post member. An elongate arm may also be provided with the instrument, the elongate arm being coupled with the post member and also being pivotal with respect to such post member. Lastly, a clamp may be engaged with the elongate arm for connecting the protractor to a second portion of the external fixation device.

A third aspect of the present invention may include a method of determining an angle between a first portion and a second portion of an external fixation device. The method may comprise the steps of attaching a first end of a protractor to the first portion of the external fixation device, attaching a second end of the protractor to the second portion of the external fixation device, and determining the angle between the first and second portions of the external fixation device by viewing an angular indicator mounted to the protractor.

Specific embodiments of this third aspect may also include the steps of rotating the second portion of the external fixation device with respect to the first portion, and determining the angle between the first and second portions by viewing the angular indicator mounted to the protractor. In some instances, the first portion is a component connected to a portion of a circumference of a ring, and the second portion is a portion of a length of a strut.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents, which operate in a similar manner to accomplish a similar purpose.

Figure 1:
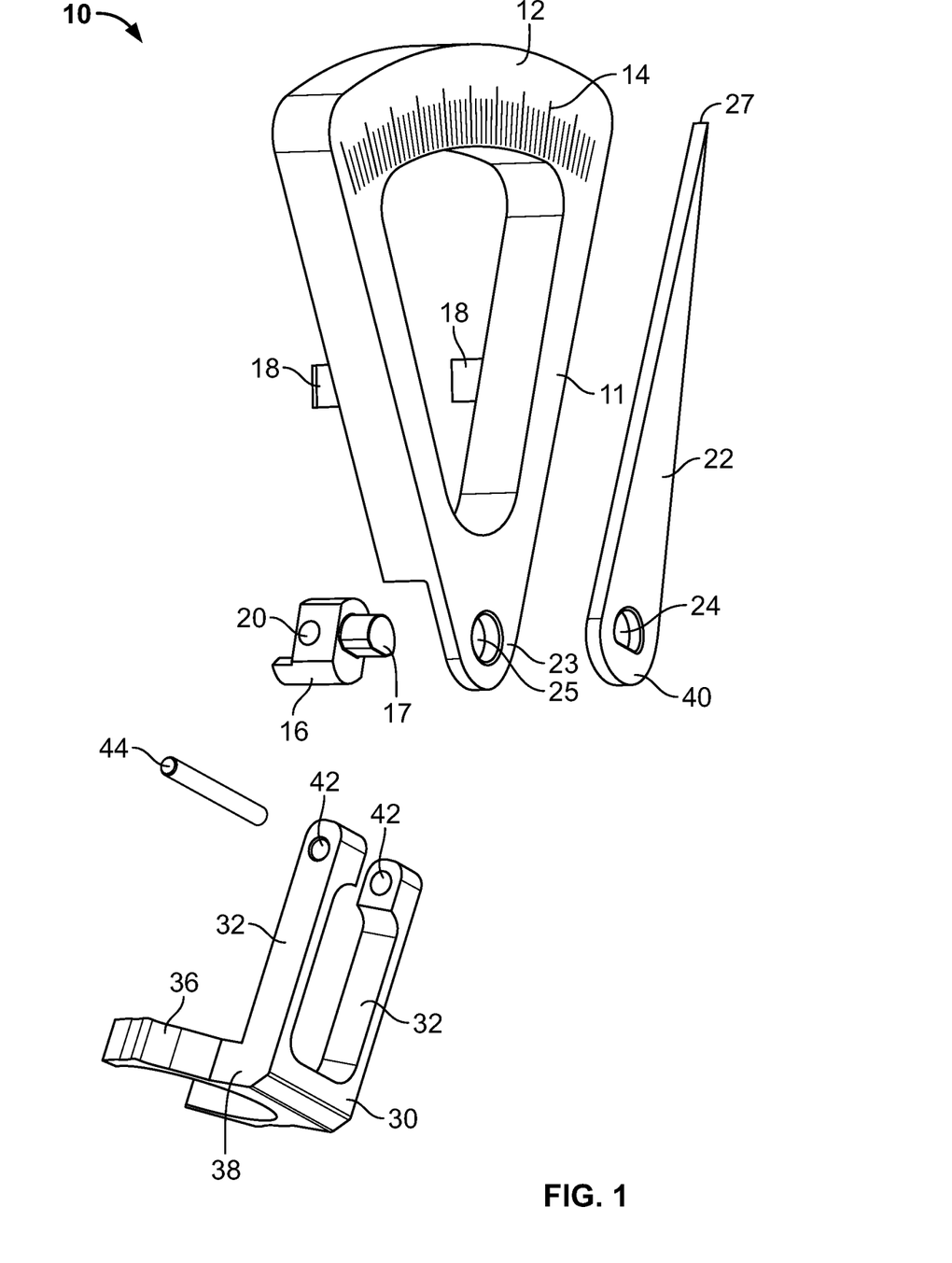
FIG. 1 is an exploded perspective view of a device for use with an external fixation frame, in accordance with one embodiment of the present invention.

Referring to FIG. 1, a device 10 may include several elements, among which may be: (1) a protractor member 11 having a face 12 with angle designations 14 thereon; (2) a rotatable dial 22 rotatably engaged or mounted to the face 12; and (3) an elongate member 30 having arms 32 projecting therefrom and an opposing clamp 36 coupled thereto. In use, device 10 may be positioned on an external fixation frame to determine the angle between two respective portions or points on such frame, as described more fully below.

Figure 2A:
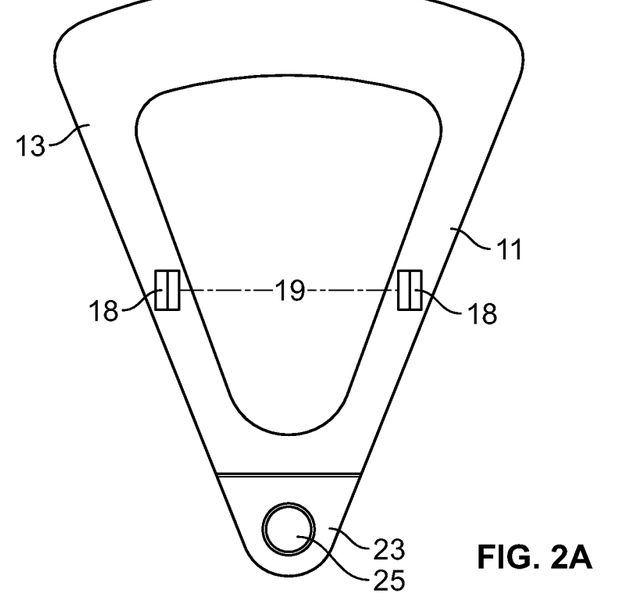
FIG. 2A is a back view of a face included with the device of FIG. 1.

Referring to FIG. 2A, the face 12 of protractor member 11 may include a set of flanges or projections 18 preferably projecting outwardly from a back or first surface thereof, the projections 18 being configured to connect device 10 to one portion or point on an external fixation frame, as alluded to above. These flanges or projections 18 may, in one embodiment, project outwardly from first surface 13 of face 12 to form a channel 19, which may accommodate a number of different structural portions of an external fixation frame (e.g., a ring portion of the frame, a component connected to such ring portion, etc.).

Figure 2B:
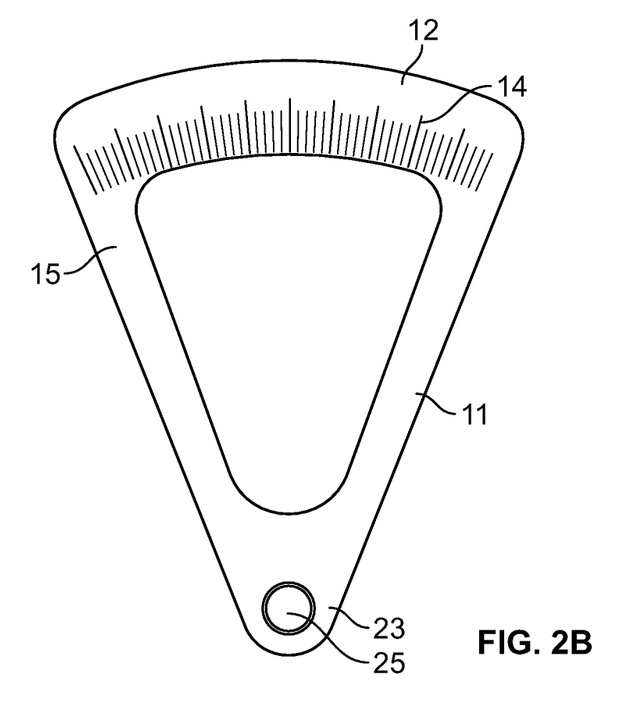
FIG. 2B is a front view of the face of FIG. 2A.
Figure 7:
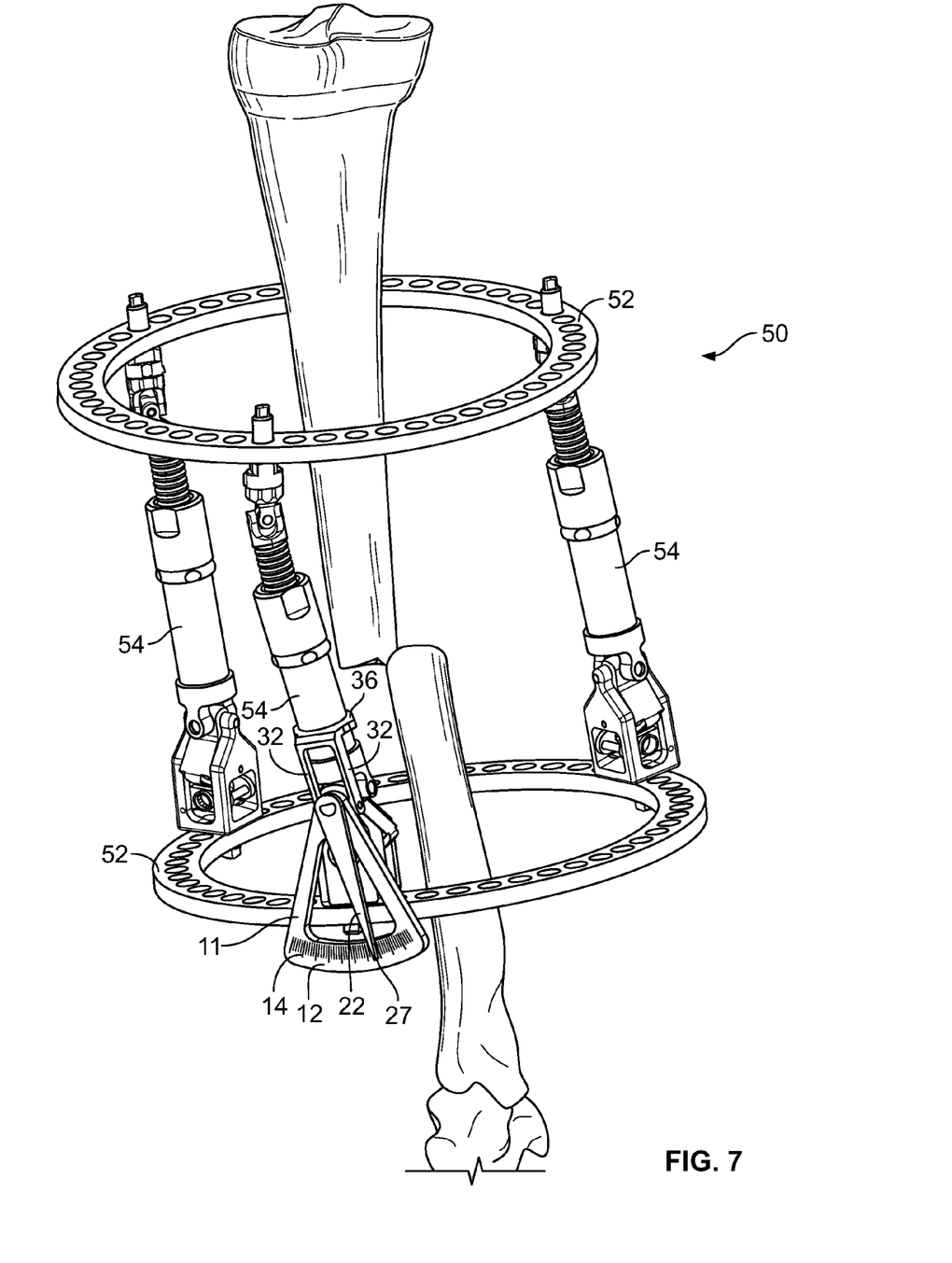
FIG. 7 is a perspective view of the device of FIGS. 1 and 6 positioned on an external fixation frame, in accordance with one embodiment of the present invention.

Flanges 18 may also be arranged, in one embodiment, at an angle perpendicular to first surface 13 of face 12. Stated differently, first and second surfaces 13, 15 of face 12, as shown in FIGS. 2A and 2B combined, may be defined by a plane extending parallel to such surfaces, and flanges or projections 18 may extend from the first surface 13 of face 12 at an angle perpendicular to that plane. In this embodiment, flanges 18 may be configured to interact with a portion of a ring 52 on an external fixation frame 50 (or another component connected to such ring 52), as best shown in FIG. 7. Thus, the flanges 18 of protractor 10 may be mounted, in one embodiment, to a ring portion 52 of an external fixation frame (or a component connected thereto) so as to determine the angle between such portion 52 and a strut 54 of the frame.

As shown in FIG. 2B, face 12 of protractor member 11 may also include angular indicia 14 thereon. Such angular indicia 14 may range from, for example, anywhere between fifteen (15) to one-hundred and sixty (160) degrees, from anywhere between zero (0) to one-hundred and eighty (180) degrees, or from anywhere between zero (0) to three-hundred and sixty (360) degrees. As an example, protractor member 11 may generally be in the shape of a triangle having an arced portion adjacent angular indicia 14, such angular indicia ranging from about eighty five (85) to one-hundred and fifteen (115) degrees.

Alternatively, in other embodiments, protractor member 11 may have a face 12 forming a complete circle, which may have angular indicia 14 thereon ranging from about zero (0) to three-hundred and sixty (360) degrees. Faces 12 forming even other shapes are also contemplated, such as a face 12 forming less than a half-circle or a face 12 forming less than a full circle. As such, due to the range of angular indicia 14 on the above-described faces 12, a surgeon or other operator may determine any angle between two or more portions or points on an external fixation frame, as described in detail below.

Figure 3:
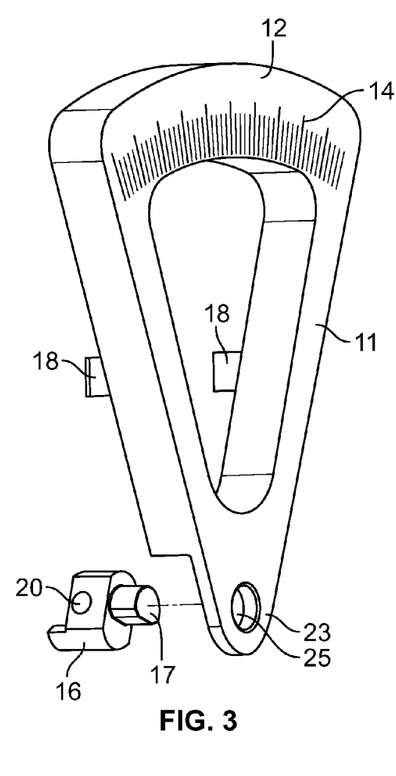
FIG. 3 is a perspective view of a post member of the device of FIG. 1, shown as being inserted into a portion of the face of the device.

Referring to FIGS. 1 and 3, the face 12 of protractor member 11 may also be configured to receive a post member 16. In one embodiment, as illustrated in FIG. 3, post member 16 may be received within a mount portion 23 projecting from a bottom portion of the protractor member 11, and specifically through an aperture 25 formed in such mount portion 23. Post member 16 may also, in a particular embodiment, include a cylindrically-shaped protrusion 17 for securing to a portion of face 12 and dial 22. The protrusion 17 may be inserted through aperture 25 in mount portion 23 and through an aperture 24 in dial 22, as shown best in FIG. 4. Post member 16 may further contain a bore 20 through a body of post member 16 for receiving a pin.

Figure 4:
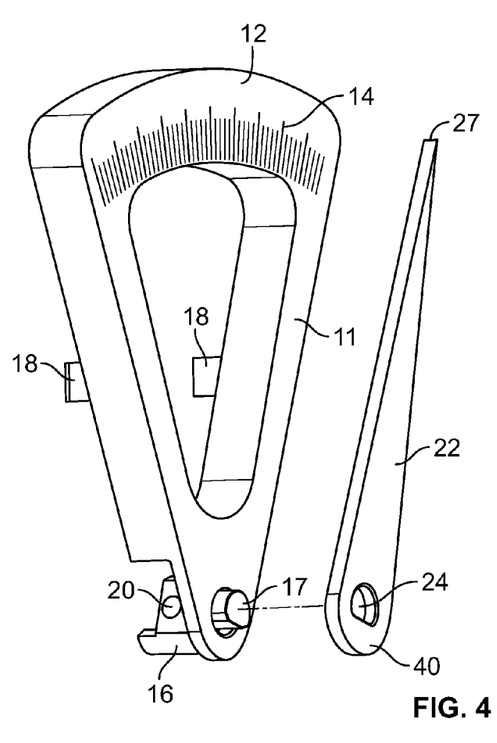
FIG. 4 is a perspective view of FIG. 3 shown with a dial being inserted over a portion of the post member.

Referring now to FIG. 4, a rotatable dial 22 having a tip 27 for pointing to specific angular indicia 14 on face 12 may be inserted over post member 16, and particularly over cylindrically-shaped protrusion 17. The rotatable dial 22 may further contain an aperture or bore 24 running through a base portion 40 of the dial 22, which may have dimensions sized to fit over the protrusion 17. In other words, base portion 40 of dial 22 may be inserted, via aperture or bore 24, over the protrusion 17 received within face 12. Here, protrusion 17 and bore 24 may each include axes that are coaxial to each other when dial 22 is mounted to post member 16. Further, protrusion 17 is shaped such that rotation of protrusion 17 within bore 24 is precluded. As such, rotation of dial 22 may necessarily cause rotation of post member 16, that is, once dial 22 is inserted over post member 16.

As further shown in FIG. 4, after insertion of the base portion 40 of dial 22 over protrusion 17 on post member 16, such elements may be secured together via compression between protrusion 17 and aperture or bore 24 through dial 22; or alternatively through the use of a bonding mechanism, such as, for example, an adhesive. Stated differently, slight differences in dimensions between protrusion 17 and aperture 24 may cause compression to result therebetween once dial 22 is inserted over post member 16. Alternatively, the use of an adhesive or other bonding mechanism may secure dial 22 to post member 16. Thereafter, rotation of dial 22 may cause rotation of post member 16, as described.

Upon inserting dial 22 over post member 16 in the manner described above, dial 22 may be securely rotated three-hundred and sixty (360) degrees in conjunction with post member 16. Thus, in a particular embodiment, rotatable dial and corresponding tip 27 may be oriented at any angle between zero (0) and three-hundred and sixty (360) degrees. As such, rotatable dial 22 and tip 27 may accommodate a face 12 having varying angular indicia 14 thereon, including a face 12 having a range of angular indicia 14 anywhere between zero (0) and three-hundred and sixty (360) degrees.

Figure 5:
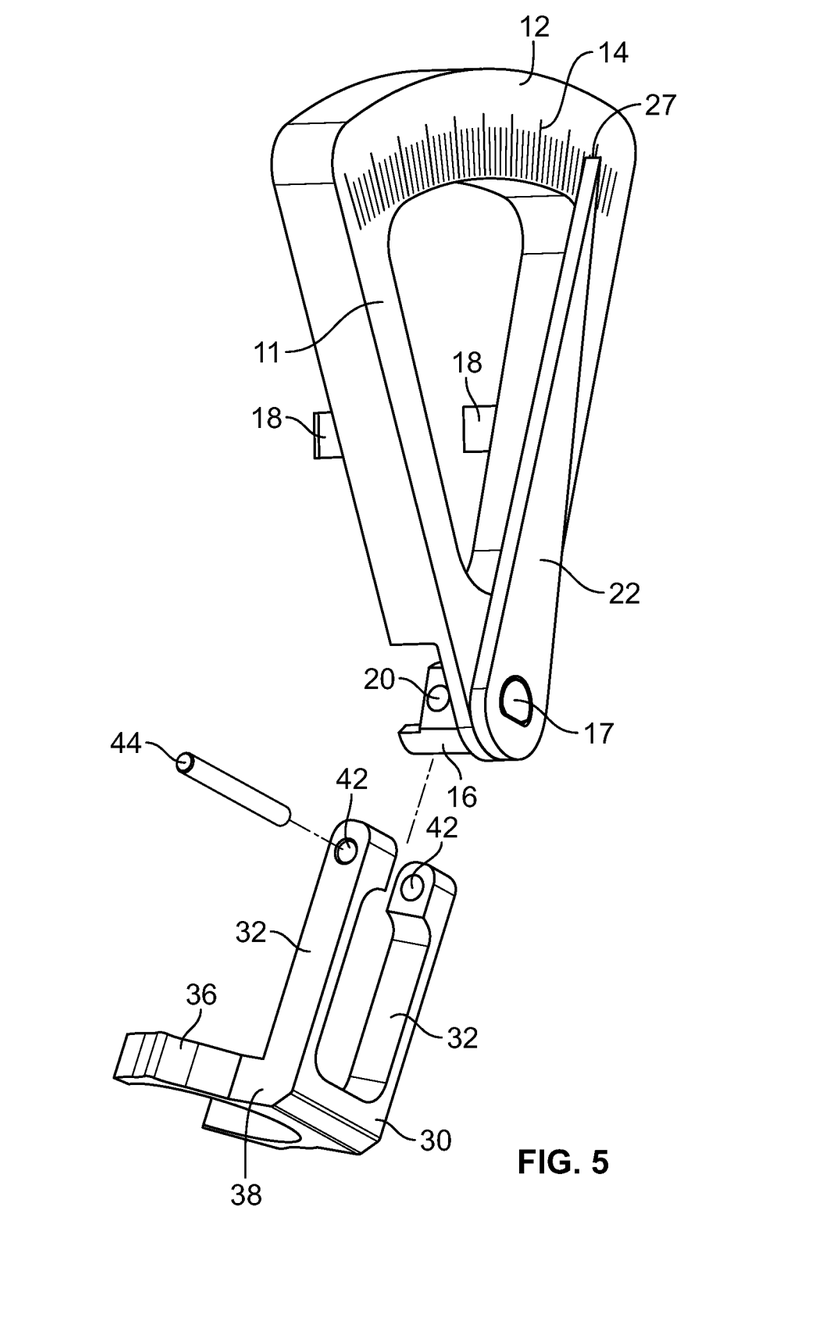
FIG. 5 is a perspective view of FIG. 4 shown with an elongate member and pin being inserted into the device.

Referring to FIGS. 1 and 5, an elongate member 30 may be pivotally connected to a portion of post member 16 (and thus to rotatable dial 22) through the use of a pair of projecting arms 32. Each such arm 32, as shown in FIG. 5, may include an aperture or bore 42 through a distal end of the arm 32, such bores 42 being aligned with the bore 20 formed through post member 16 upon assembly. In a particular embodiment, projecting arms 32 may be connected to post member 16 by use of a pin or clip 44 inserted into apertures 42 and through bore 20.

Figure 6:
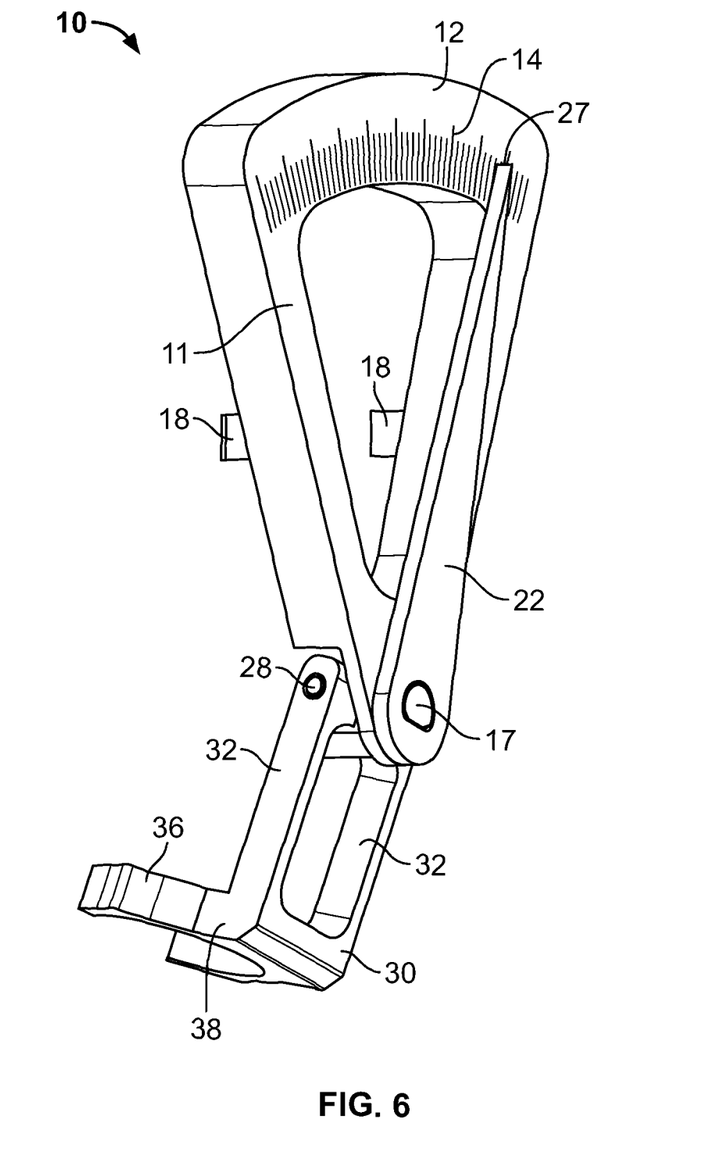
FIG. 6 is an assembled perspective view of the device of FIG. 1.

Once securely connected to post member 16 (and thus rotatable dial 22), the elongate member 30 may pivotally adjust or translate about respective hinge points 28, as shown in FIG. 6, which may be located at the connection between projecting arms 32 and post member 16. Accordingly, rotatable dial 22 and elongate member 30 may rotate in conjunction with post member 16, and elongate member 30 may also pivot about hinge points 28. Thus, elongate member 30 may be positioned at various different locations within separate axes (e.g., the axis of rotation about post member 16, and the axis of rotation about hinge points 28). Stated differently, elongate member 30, due to its connection with post member 16, may rotate in conjunction with dial 22 and pivot about hinge points 28; and, therefore may have multiple degrees of freedom with which to rotate and/or pivot.

Referring now to FIGS. 1 and 6, arranged on an opposing end of elongate member 30, may be a clamping or retaining means 36. In a particular embodiment, clamping or retaining means 36 may be in the form of a semi-circular ring. The ring 36 may also be sized such that it may grasp a cylinder or post, as is typically found in a strut 54 of an external fixation frame 50 as shown, for example, in FIG. 7. Clamp 36 may also include a connection point 38 with elongate member 30, which in one embodiment may arrange clamp 36 at perpendicular angle with respect to the longitudinal axis of elongate member 30. As a result, upon assembly of the protractor-type device 10, as shown in FIG. 6, each of rotatable dial 22 and elongate member 30 may be fully pivoted about their respective connection points (e.g., for rotatable dial 22—aperture 24 with protrusion 17 on post member 16; and for elongate member 30—projecting arms 32 with post member 16 via pin 44). Such pivotal connections allow the protractor-type device 10 to measure the angle between respective points on an external fixation frame 50, as discussed more fully below with respect to FIG. 7.

Referring to FIG. 7, in use, device 10 may be configured to measure the angle between two or more respective points on an external fixation frame 50. In one embodiment, the external frame 50 used may be structurally similar to that found in U.S. Patent App. Pub. No. 2010/0234844, the disclosure of which is incorporated by reference herein in its entirety. Other well known external fixation frames may also be used with device 10. Further, external fixation frame 50 may be adjusted in a similar manner to the methods described in U.S. Ser. No. 13/167,101 (hereinafter referred to as "the '101 Application") filed Jun. 23, 2011, the disclosure of which is hereby incorporated by reference in its entirety. Thus, in general, the external fixation frame 50 may comprise two circular rings 52 connected together by way of several struts 54. In one embodiment, the rings 52 may be placed about a patient's leg, or other injured appendage, and the struts 54 may provide stabilization between such rings 52. Accordingly, the external fixation frame 50 may be connected to an injured site of a patient and used to stabilize the injury. In some embodiments, the length of the struts may be adjusted manually or a predetermined amount via a hand held motorized tool. In either case, protractor member 11 may be used to measure the angle and change thereof between a strut and an adjacent ring 52. Typically, such external fixation frames 50 are used to stabilize serious fractures or dislocations of bone, thus facilitating healing of the damaged bone.

To measure the angle between two or more points on external fixation frame 50, flanges or projections 18 on face 12 of the protractor member 11 may first be inserted over a portion of a ring 52 (or another component connected to such ring 52). More particularly, the channel 19 formed by flanges 18 may be oriented adjacent a portion of a ring 52 (or another component connected to such ring 52) and may then be inserted over such portion 52 (or component), thus allowing flanges 18 to surround and grasp the ring 52 (or other component). Once flanges 18, and by extension protractor member 11, are secured to a portion of ring 52 on external fixation frame 50 (via connection with the ring 52 or other component), the clamp 36 on elongate member 30 may be connected to a separate portion of external fixation frame 50, such as, for example, a strut 54 of the frame 50. Specifically, an open end of clamp 36 may be arranged adjacent a strut 54 and may be inserted over the strut 54, causing the clamp 36 to expand in response to the increased dimensions of strut 54, and then to contract and surround strut 54 upon full insertion. At this point, the device or protractor 10 may be connected to a ring portion 52 (or other component connected to such ring 52) of external fixation frame 50 via flanges 18, and to a strut 54 of the frame 50 via clamp 36.

With the device 10 connected to external fixation frame 50 as described, the dial 22 on face 12 and the elongate member 30 may remain fully pivotal about their respective connection points (e.g., for rotatable dial 22—aperture 24 with protrusion 17 on post member 16; and for elongate member 30—projecting arms 32 with post member 16 via pin 44). Accordingly, a surgeon, nurse, or other skilled practitioner, as well as a patient alone, may adjust the external fixation frame 50 to a desired orientation while device 10 is attached thereto. In other words, with device 10 connected to the external fixation frame 50, and the frame 50 secured to a patient, an operator may adjust the frame 50 while viewing the particular orientation of dial 22 with respect to angular indicia 14. Once tip 27 of rotatable dial 22 reaches a desired point, the operator may cease in moving frame 50 and secure the frame 50 accordingly.

As an example, and merely for illustrative purposes, upon connecting device 10 to external fixation frame 50 in the manner described above, the initial angle between a portion of ring 52 and a strut 54 may be thirty (30) degrees, while an optimal angle between ring 52 and strut 54 may be forty (40) degrees. To change the initial angle referred to above, a surgeon, nurse, other skilled operator, or a patient alone may simply adjust external fixation frame 50 with protractor-type device 10 attached, thus causing rotatable dial 22 to pivot in the appropriate direction, and settle at an angle of forty (40) degrees. An optimal angle between strut 54 and ring 52 of external fixation frame 50 may thusly be achieved, and the patient to whom the frame 50 is attached may experience improved stabilization and healing at the injury site. Subsequently, should the angle between strut 54 and ring 52 of the external fixation frame 50 need to be adjusted, a surgeon, nurse, or other skilled practitioner may simply re-attach the protractor-type device 10 to the frame 50 and adjust the fixation frame 50 accordingly. Follow up visits with the patient for this purpose may be routine, due to the fact that the external fixation frame 50 may move from desired or optimal orientations during normal use.

The aforementioned device 10 may also be utilized by a patient in conjunction with an instrument for properly adjusting an external fixation frame, as described in the '101 Application. Such interaction is briefly described below.

As disclosed in the '101 Application, a tool, which may be referred to as a "smart tool," includes, inter alia: (1) a driver for engaging a screw or screws on an external fixation frame; (2) a motor for actuating the driver, (3) a memory for receiving data; and (4) a processor for executing applications. In a particular embodiment, the memory of the smart tool may be configured to receive a "correction plan" for the patient being treated. For example, a computer program, utilizing software and the input of a trained practitioner, may create a "correction plan" for a patient. The correction plan generated may include a computer rendering of the various positions for the external fixation frame during treatment. As a specific example, the "correction plan" may include an optimal position for the external fixation frame at day five (5) of treatment, and an optimal position for the external fixation frame at day ten (10) of treatment.

Once the aforementioned "correction plan" is generated, it may thereafter be stored into the smart tool of the '101 Application via the "memory" of the tool. The tool can then be used by the patient to adjust the external fixation frame according to the parameters of the correction plan. This adjustment is described in detail in the '101 Application. Briefly summarizing, a patient may engage the driver of the smart tool with a screw on the external fixation frame, which may be rotated via the motor of the smart tool. The smart tool may then rotate the driver until the screw, and by extension the frame, reaches an optimal position, which corresponds to the "correction plan" developed. The smart tool may then emit an alarm or sound indicating that adjustment is complete, that is, once the "memory" of the smart tool determines that an optimal position for the frame, according to the "correction plan" entered, has been reached.

This adjustment method, as described, may therefore change the orientation of a particular strut with respect to one (or both) of the rings of the external fixation frame used. In some instances, it may be useful to verify that this change in angle is correct, in terms of the "correction plan" developed. The device or protractor 10 as hereinbefore described may be useful for this purpose, and may provide a patient with a means for ensuring that the "correction plan" is properly adhered to. Thus, upon adjustment of an external fixation frame with the smart tool, as set forth in the '101 Application and briefly described above, a patient may connect device 10 to two points on the external fixation frame. The patient may then verify the angle between both such points, so as to ensure the proper orientation for the external fixation frame, in terms of the treatment plan (i.e., the correction plan) created.

In the devices shown in the figures, particular structures are shown as being adapted for measuring an angle between two or more points on an external fixation frame, or other similar device. The invention also contemplates the use of any alternative structures for such purposes, including structures having different lengths, shapes, and configurations. For example, while the device 10 has been described as being used with an external fixation frame 50 similar to that disclosed in U.S. Patent App. Pub. No. 2010/0234844, device 10 may be used with various other types of external fixation frames known in the art.

Moreover, with respect to flanges or projections 18 extending from face 12 of device 10, it is contemplated that the same, while not including such features in the main embodiment discussed above, may include a set of protrusions extending in a direction towards channel 19 for securing each respective flange portion 18 to a segment of the external fixation frame 50. In this regard, although in one embodiment flanges 18 may include a pair of protrusions, one such protrusion on each respective flange 18, it is equally contemplated that flanges 18 may also have additional protrusions. In other embodiments, flanges 18 may lack protrusions, as described above in the main embodiment, and device 10 may be secured to a portion of an external fixation frame via the relative dimensions of such portion and channel 19 formed by flanges 18. For example, channel 19 may have a width that is slightly less than the width of a portion of the external fixation frame to which protractor member 11 is attached (e.g., via flanges 18). Due to this difference in dimensions, device 10 may be securely held in place on the external fixation frame via a compressive force between flanges 18 and the portion of the external fixation frame to which device 10 is engaged to.

As another example, while flanges 18 may, in one embodiment, be oriented perpendicular to face 12, it should be appreciated that flanges 18 may also be arranged obliquely to face 12. Thus, flanges 18 may be angled at any obtuse or acute angle with respect to face 12. Even further, flanges 18 may also include a curvature, as opposed to being linear as depicted in the figures. Stated differently, any particular shape or orientation for flanges 18 is contemplated, provided that such flanges 18 can securely attach to a portion of external fixation frame 50, such as a portion of a ring 52 (or other component connected to such ring 52).

Further still, while post member 16 has been described as having a protrusion 17 that is cylindrical in shape, alternate shapes for protrusion 17 are contemplated, such as rectangular, triangular, or rhomboidal. In any instance, protrusion 17 on post member 17 should be configured to rotate fully within the aperture 24 formed in mount portion 23 of face 12 so that dial 22 may rotate with respect to face 12.

It is further contemplated that, while protrusion 17 on post member 16 has been described as being stationary, protrusion 17 may be fully rotatable. Stated differently, post member 16 may be connected to dial 22, such that both components are independently rotatable with respect to one another via rotatable protrusion 17. In still other embodiments, stop members (not shown) may be provided on either dial 22 and/or post member 16, which lock protrusion 17 with respect to dial 22, such that both components may rotate in conjunction with one another if desired.

Additionally, although device 10 has been described as using an analog readout (i.e., angular indicia 14), it is fully contemplated that device 10 may utilize a digital readout. Thus, instead of utilizing angular indicia 14 on face 12, device 10 may utilize a digital readout, which displays the particular angle of dial 22 in digital form. This digital readout may serve to improve the accuracy with which device 10 measures angles, and may also provide easier readability for a user of device 10.

Further, although clamp 36 has been described as being integrally formed with elongate member 30, and at a perpendicular angle with respect to the longitudinal axis of such member 30, clamp 36 may be a separate piece that is connected to elongate member 30 via a pin arrangement and/or may be set at any oblique angle with respect to the longitudinal axis of elongate member 30. As such, in some embodiments, clamp 36 may pivot about or otherwise be angled with respect to the longitudinal axis of elongate member 30 (e.g., via a pin connection between clamp 36 and elongate member 30, or through angling clamp 36 obliquely to elongate member 30). In yet other embodiments, alternate pivotable connections are also contemplated. For instance, a ball-and-socket arrangement, which couples clamp 36 to elongate member 30, may be used. Specifically, either of clamp 36 or elongate member 30 may contain a ball or spherical member, and the other of clamp 36 or elongate member 30 may contain a corresponding socket member for receiving the aforementioned ball. Upon connecting these two components (e.g. inserting a ball on clamp 36 into a socket on elongate member 30), clamp 36 may be fully rotatable or pivotable about the connection point. Thus, clamp 36 may be fully pivotable in different directions. Still other connection points providing for rotation and pivoting of clamp 36 are contemplated, as is known in the art.

It is also contemplated that the above-described ball-and-socket arrangement may be used for the connection between elongate member 30 and post member 16. Even further, it is also contemplated that a portion of elongate member 30 may be rotatable so as to allow easier positioning of clamp 36. More specifically, a first portion of elongate member 30 may be coupled to a separate second portion of elongate member 30, such that the first portion is configured to rotate with respect to the second portion, preferably along a longitudinal axis of the elongate member 30. Thus, the second portion of elongate member 30 (or first portion, depending), may spin with respect to the first portion (or second portion) about a longitudinal axis of the elongate member 30. Such rotatable characteristics may, in one embodiment, permit a user of the device 10 to more easily secure clamp 36 to a strut of an external fixation frame.

While clamp 36 has also been described as being in the shape of a semi-circular ring, clamp 36 may alternatively be in the shape of an open diamond-type structure in which the open end of the structure may be inserted over a strut 54 of an external fixation frame 50. Similarly, an open rectangular-type structure is also contemplated, in which the open end of such structure may be inserted over a strut 54 of an external fixation frame 50, and projections at such open end may wrap around the strut. Many different structures are therefore contemplated for the configuration of clamp 36, provided that such structures are capable of grasping a strut 54 or other portion of an external fixation frame 50.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. An instrument for determining an angle between a first portion and a second portion of an external fixation device comprising:
    a face having a connector for engaging the face to the first portion of the external fixation device;
    a rotatable dial mounted to the face;
    an elongate member coupled to the rotatable dial, wherein the elongate member is pivotable relative to the face within a first plane and rotatable relative to the face within a second, different plane; and
    a coupling engaged to the elongate member for connecting to the second portion of the external fixation device,
    wherein the first portion of the external fixation device is rotatably connected to the second portion of the external fixation device.

2. The instrument of claim 1, wherein the face is arced and has angle designations thereon extending from 85° to 115°.

3. The instrument of claim 1, wherein the connector on the face includes a set of opposed and extending flanges, the flanges defining a channel sized to receive the first portion of the external fixation device.

4. The instrument of claim 1, wherein the first portion of the external fixation device is a component connected to a portion of a circumference of a ring.

5. The instrument of claim 1, wherein the rotatable dial is mounted to a post member extending outwardly from the face of the instrument.

6. The instrument of claim 5, wherein the dial is rotatable in conjunction with the post member.

7. The instrument of claim 1, wherein the elongate member is pivotally coupled to the rotatable dial via a hinge connection.

8. The instrument of claim 1, wherein the coupling is a semi-circular clamp sized to engage the second portion of the external fixation device.

9. The instrument of claim 8, wherein the second portion of the external fixation device is a portion of a length of a strut.

10. An instrument for use with an external fixation device comprising:
    a face with a plurality of angle designations thereon;
    a connector for engaging the face to the external fixation device, the connector including opposed projections spaced apart from one another, such that the projections are attachable to a first portion of the external fixation device;
    a rotatable dial mounted to a post member engaged with the face, the dial being rotatable in conjunction with the post member;
    an elongate arm coupled with the post member, the arm being pivotal with respect to such post member; and
    a clamp engaged with the elongate arm for connecting the instrument to a second portion of the external fixation device.

11. The instrument of claim 10, wherein the elongate arm is pivotable relative to the face within a first plane and rotatable relative to the face within a second, different plane.

12. The instrument of claim 10, wherein the clamp is a semi-circular clamp sized to engage the second portion of the external fixation device.

13. The instrument of claim 12, wherein the second portion of the external fixation device is a portion of a length of a strut.

\* \* \* \* \*